US00PP08965P

United States Patent [19]

Heims

[11] Patent Number: Plant 8,965

[45] Date of Patent: Nov. 1, 1994

[54] HEUCHERA CHOCOLATE RUFFLES

[75] Inventor: Dan M. Heims, Portland, Oreg.

[73] Assignee: Terra-Nova Nurseries, Inc., Portland, Oreg.

[21] Appl. No.: 176,134

[22] Filed: Dec. 30, 1993

[51] Int. Cl.[5] ..... A01H 5/00
[52] U.S. Cl. ..... Plt./68.1
[58] Field of Search ..... Plt. 68.1

*Primary Examiner*—James R. Feyrer
*Attorney, Agent, or Firm*—Klarquist Sparkman Campbell Leigh & Whinston

[57] ABSTRACT

A new and distinct hybrid of Heuchera characterized by unique, ruffled leaves of chocolate coloration showing the burgundy underside through the ruffles.

2 Drawing Sheets

The present invention relates to a new and distinct hyrbid of Heuchera which originated as a cross-pollination of Heuchera "Pewter Veil" and *Heuchera micrantha* "Ruffles" in the Saxifragaceae family.

The new Heuchera is a result of a controlled cross of the aforementioned plants at a Terra-Nova Nursery, Inc., in Portland, Oreg. This hybrid was selected from a large selection of seedlings. Mother plants were retained to observe habit and to compare with their progeny. The new variety has been reproduced only be asexual propagation (division and tissue culture). Each of the progeny exhibits identical characteristics to the original plant and is unlike any Heuchera offered by any American nursery or book as evidenced by the following characteristics:

(1) Summer, fall and winter: Chocolate-Olive coloration on the ruffled foliage. Reverse shown.

(2) Spring: Foliage of a warm Chocolate Brown on ruffled foliage with a Burgundy reverse.

Asexual propagation by division and tissue-culture as done in Mt. Vernon, Wash., shows that the foregoing characteristics and distinctions come true to form and are established and transmitted through succeeding propagations.

BRIEF DESCRIPTION OF THE PHOTOGRAPHS

DETAILED PLANT DESCRIPTION

Figure 1:
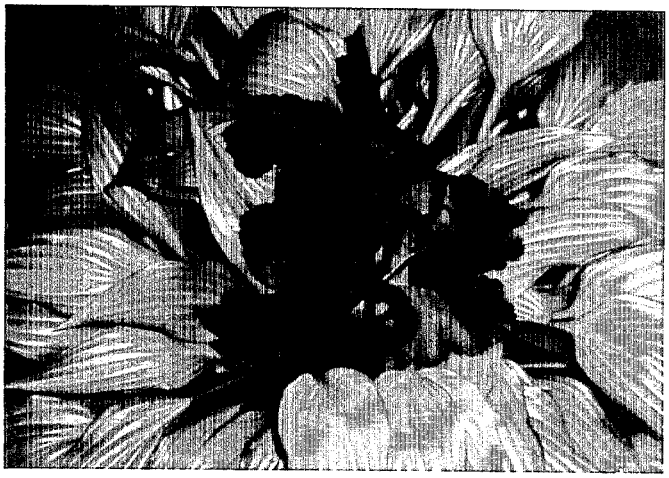
FIG. 1 is a spring picture showing the relative leaf size against Hosta "Chinese Sunrise".
Figure 2:
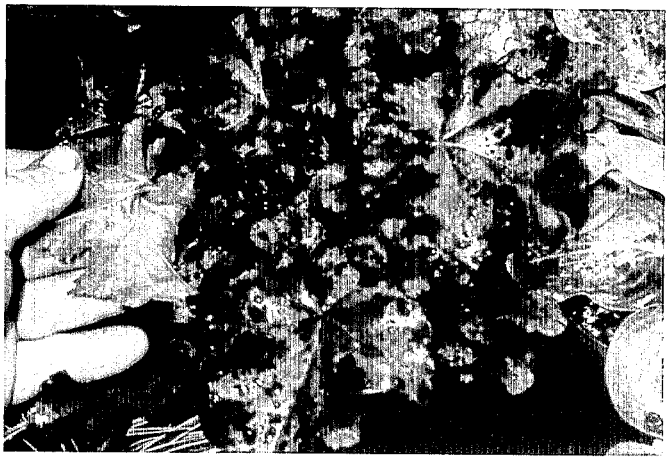
FIG. 2 is a picture of the maroon obverse of the leaf.
Figure 3:
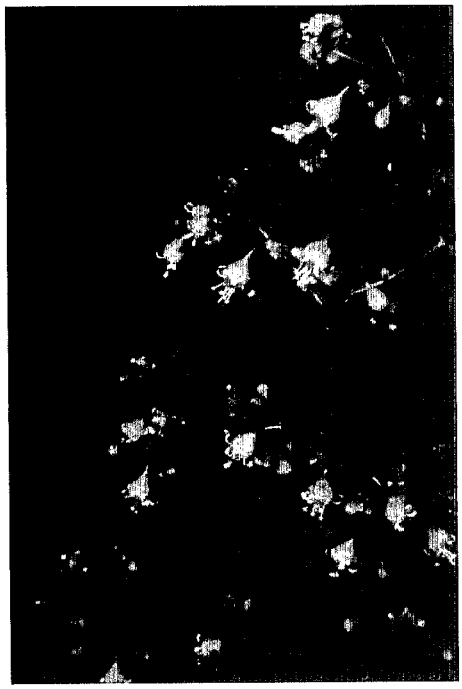
FIG. 3 is a picture of the plant in flower.

The following is a detailed description of the new Heuchera hybrid based on observations of specimens in Portland, Oreg. The color descriptions are all based on The Royal Horticultural Society Color Chart.

Foliage:

*Type.*—Evergreenm herbaceous in a hard winter.
*Shape.*—Rounded undulate-cordate, 9-lobed.
*Length.*—14 to 22 cm ($5\frac{1}{2}$ to 9 in).
*Width.*—14 to 22 cm ($5\frac{1}{4}$ to 9 in).
*Petiole length.*—14 to 20 cm ($5\frac{1}{2}$ to 8 in).
*Margins.*—Undulate-crenate, ciliolate.
*Apex.*—Broadly obtuse, lobed.

*Base.*—Cordate.
*Texture.*—Slightly rugose, glabrous.
*Leaf arrangement.*—Basal leaves tufted.
*Venation.*—Reticulate.

Flower:

*Petal count.*—5 petals.
*Petal shape.*—Spatulate, recurved. Entire margin.
*Flower type.*—Complete, calyx tube urn-shaped, stamens exserted.
*Flower size.*—0.75 to 1.0 cm (0.3 to 0.4 in).
*Flower number.*—150–250 blooms per stem.
*Blooming habit.*—Paniculate to 70 cm.
*Bloom period.*—May to July.

Color Characteristics

Foliage:

*Mature leaves upper surface.*—Spring: Yellow-Green Group 147A, overlaid by Greyed-Orange Group 166B.
*Upper surface, summer through winter.*—Yellow-Green Group 147A.
*Lower surface.*—Red-purple Group 71A.

Flowers: White, recurved calyx, Yellow-Green Group 145D on paniculate stems of Red-Purple Group 71A. Flowers may number several hundred per stem.

DESCRIPTION OF PARENT PLANTS

This Heuchera hybrid has characteristics which make it unique from its parents: Heuchera "Pewter Veil" and *Heuchera micrantha* "Ruffles". *Heuchera micrantha* "Ruffles" is described in the Terra-Nova Nursry's catalog as having heavily ruffled, hirsute foliage and white panicles of flowers. Heuchera "Pewter Veil" is described in the same catalog as a cross between Heuchera "Montrose Ruby" and *Heuchera americana* "Dale's Strain". The ensuing plants have pink/bronze-metallic leaves with pronounced veining. No other Heuchera in commerce resembles Heuchera "Chocolate Ruffles".

I claim:

1. A new and distinct hybrid of Heuchera substantially as shown and described, characterized by unique, ruffled leaves of chocolate coloration showing the burgundy underside through the ruffles.

* * * * *